(12) United States Patent
Lowe et al.

(10) Patent No.: US 9,642,581 B2
(45) Date of Patent: *May 9, 2017

(54) SPECIMEN RADIOGRAPHY WITH TOMOSYNTHESIS IN A CABINET

(71) Applicant: KUB TECHNOLOGIES, INC., Milford, CT (US)

(72) Inventors: Chester Lowe, Stamford, CT (US); Vikram Butani, Fairfield, CT (US); Tim Ely, Fairfield, CT (US)

(73) Assignee: KUB Technologies, Inc., Stratford, CT (US)

( * ) Notice: Subject to any disclaimer, the term of this patent is extended or adjusted under 35 U.S.C. 154(b) by 129 days.

This patent is subject to a terminal disclaimer.

(21) Appl. No.: 14/262,829

(22) Filed: Apr. 28, 2014

(65) Prior Publication Data

US 2015/0131778 A1    May 14, 2015

Related U.S. Application Data

(60) Provisional application No. 61/902,878, filed on Nov. 12, 2013.

(51) Int. Cl.
*A61B 6/00* (2006.01)
*A61B 6/02* (2006.01)
*A61B 6/03* (2006.01)
*G01N 23/04* (2006.01)

(52) U.S. Cl.
CPC ............ *A61B 6/025* (2013.01); *A61B 6/03* (2013.01); *A61B 6/032* (2013.01); *A61B 6/035* (2013.01); *A61B 6/4405* (2013.01); *A61B 6/4411* (2013.01); *A61B 6/4429* (2013.01); *A61B 6/4452* (2013.01); *A61B 6/502* (2013.01);

(Continued)

(58) Field of Classification Search
CPC ........... A61B 6/025; A61B 6/03; A61B 6/032; A61B 6/035; A61B 6/4405; A61B 6/4411; A61B 6/4429; A61B 6/4452; A61B 6/502; G01N 23/046
USPC .................. 378/22, 25, 26, 37, 196–198
See application file for complete search history.

(56) References Cited

U.S. PATENT DOCUMENTS 5,872,828 A    2/1999  Niklason et al.
6,028,910 A *  2/2000  Kirchner ............. G01N 23/046
                                                378/21

(Continued)

*Primary Examiner* — Allen C. Ho
(74) *Attorney, Agent, or Firm* — Ziegler IP Law Group, LLC (57) ABSTRACT

A method and system for producing tomosynthesis images of a breast specimen in a cabinet x-ray system. An X-ray source delivers X-rays through a specimen of excised tissue and forms an image at a digital X-ray detector. Multiple X-ray images are taken as the X-ray source moves relative to the stationary breast specimen. In the preferred embodiment, the X-ray source moves in a range from about 350° to and including about 10°. The X-ray source may travel substantially along a path that generally defines an arc, or linearly, while the digital X-ray detector remains stationary throughout and the X-ray source remains substantially equidistant from the specimen platform. The set of X-ray image data taken at the different points are combined to form a tomosynthesis image that can be viewed in different formats, alone or as an adjunct to conventional specimen radiography.

32 Claims, 7 Drawing Sheets

(52) U.S. Cl.
CPC ......... *A61B 6/5217* (2013.01); *G01N 23/046* (2013.01); *G01N 2223/309* (2013.01)

(56) References Cited

U.S. PATENT DOCUMENTS

| | | | |
|---|---|---|---|
| 6,236,708 B1 * | 5/2001 | Lin | A61B 6/025 378/22 |
| 6,324,249 B1 * | 11/2001 | Fazzio | G01N 23/04 378/22 |
| 7,020,243 B2 * | 3/2006 | Hsieh | A61B 6/032 378/156 |
| 7,120,283 B2 * | 10/2006 | Thieret | G06T 11/006 128/922 |
| 7,356,113 B2 * | 4/2008 | Wu | A61B 6/025 378/22 |
| 7,463,713 B2 * | 12/2008 | Mertelmeier | A61B 6/025 378/22 |
| 7,545,907 B2 * | 6/2009 | Stewart | A61B 6/02 378/108 |
| 7,708,462 B2 * | 5/2010 | Fujiwara | A61B 6/025 378/206 |
| 7,778,388 B2 * | 8/2010 | Sendai | A61B 6/025 378/22 |
| 8,005,184 B2 * | 8/2011 | Chen | A61B 6/032 378/21 |
| 8,184,765 B2 * | 5/2012 | Akahori | A61B 6/032 378/25 |
| 8,284,894 B2 * | 10/2012 | Poorter | A61B 6/025 378/21 |
| 8,363,050 B2 * | 1/2013 | Ludwig | A61B 6/025 345/419 |
| 8,559,593 B2 * | 10/2013 | Akahori | A61B 6/032 378/115 |
| 8,675,814 B2 * | 3/2014 | Akahori | A61B 6/032 378/196 |
| 8,798,231 B2 * | 8/2014 | Notohara | A61B 6/025 378/22 |
| 8,848,864 B2 * | 9/2014 | Jeong | G01N 23/046 378/21 |
| 9,138,193 B2 * | 9/2015 | Lowe | A61B 6/502 |
| 2008/0232545 A1 | 9/2008 | Wu et al. | |
| 2013/0064437 A1 | 3/2013 | Meetz | |
| 2013/0272494 A1 | 10/2013 | DeFreitas et al. | |

\* cited by examiner

Fig. 1

FRONT VIEW INTO CABINET
Door Open
Fig 2

Fig. 3

Typical Example of an X-ray Cabinet System
Fig. 4

View in Sample Chamber with Door Open with
X-ray source at position (14) Top Center
Fig. 5

Lateral View of X-Ray Source
Mounted to Swing Arm at position (14)
Fig. 6

Fig. 7A - Top Slice – 59m

Fig. 7B - Bottom Slice – 13.5 mm

Fig. 7C - Middle Slice – 30.5 mm

Images of an Apple at multiple depth cuts
after tomosynthesis reconstruction from bottom up with the bottom at 0mm

SPECIMEN RADIOGRAPHY WITH TOMOSYNTHESIS IN A CABINET

CROSS-REFERENCE TO RELATED APPLICATIONS

This application claims priority to and the benefit of U.S. Provisional Patent Application Ser. No. 61/902,878, filed on 12 Nov. 2013, the disclosure of which is incorporated herein by reference in its entirety.

BACKGROUND

Field of the Present Disclosure

The aspects of the disclosed embodiments are directed to the field of cabinet X-ray imaging of excised human tissue, and more specifically, to a system and method for obtaining and processing cabinet X-ray image data for tomosynthesis reconstruction allowing for a three-dimensional image of the specimen.

Description of the Related Art

Imaging of a patient's tissue has become a common screening tool and/or diagnostic aid in modern medicine. Breast cancer remains a significant threat to women's health and is considered the most common cancer among women today. One strategy for dealing with breast cancer is early detection of the cancer so that it may be treated prior to the cancer metastasizing throughout the body. This causes an increase in the number of surgical procedures performed involving excision of cancerous tissue or calcifications, such as ductal carcinoma in situ (DCIS).

The excision of DCIS is a challenging task. In order to assure that the complete DCIS lump including a cancer-free margin has been excised, the following steps may be undertaken. A pre-operational planning based on mammograms is performed carefully in order to assess the size and the location of the lump. The location of the lump is marked utilizing guide wires/markers. During the lumpectomy, the excised tissue is examined using X-ray imaging in order to assess whether its margin is cancer-free. If it is found that the excised specimen has an insufficient margin of cancer-free tissue, the surgeon removes more tissue.

Currently, X-ray images obtained are only available in two-dimensional mode, and as such, orthogonal views of the sample must be obtained by physically rotating the specimen to verify the margins. The breast surgeon relies on the radiogram to verify removal of the complete lump. If necessary, the breast surgeon may have to identify additional breast tissue that must be excised to ensure a clear margin. This is an error prone and time consuming task that is performed under significant time pressure whilst the anesthetized patient is still lying on the operating table.

In typical X-ray imaging, a patient's breast sample is immobilized and contained in a specimen container. The sample is placed between an X-ray source and a digital imaging device (detector) to create a two-dimensional radiographic image of the sample. To ensure that margins are attained, at least 2 orthogonal images must be taken of the sample (90 degrees apart). The problem that arises with the above scenario is that the tissue, being somewhat fluid, may displace when it is imaged in either position, which may cause and provide a false measurement to the breast surgeon. It would be advantageous to be able to image the sample from a greater number of different positions of the source and receptor relative to the sample while maintaining the sample stationary or in a fixed position.

Digital tomosynthesis combines digital image capture and processing with simple tube/detector motion as used in conventional radiographic tomography. Although there are some similarities to CT, it is a separate technique. In CT, the source/detector makes a complete 360-degree rotation about the subject obtaining a complete set of data from which images may be reconstructed. In digital tomosynthesis, a small change of flux created by only a small rotation angle with a small number of exposures are used. This set of data can be digitally processed to yield images similar to conventional tomography with a limited depth of field. However, because the image processing is digital, a series of slices at different depths and with different thicknesses can be reconstructed from the same acquisition, saving time.

Image data taken at the different imaging positions can be processed to generate tomosynthetic images of selected slices of the sample. The images can be of thin slices, essentially planar sections through the specimen, as in CT slices. Alternatively, they can be varying thickness.

The isocenter of the image acquisition geometry is located below the sample, on the surface of the detector. The phase shifts created as a result of this arrangement are compensated for, while processing the resultant dataset. The tomosynthetic images are then generated from the generated data set.

It is believed that no cabinet specimen tomosynthesis systems are commercially available currently for clinical use in specimen imaging, and that improvements in X-ray imaging and tomosynthesis are a desired goal. Accordingly, it is believed that there is a need for improved and practical tomosynthesis of breast specimens.

It would be advantageous to have a cabinet X-ray system for specimen imaging that could create, via digital tomosynthesis, a three-dimensional image for the breast surgeon to ensure that a proper margin around the diseased tissue has been excised in an expedient manner.

SUMMARY

As described herein, the exemplary embodiments overcome one or more of the above or other disadvantages known in the art.

In one embodiment, the aspects of the present disclosure are directed to a method and system for obtaining breast specimen x-ray images, projection tomosynthesis x-ray images, and reconstructed tomosynthesis x-ray images of a patient's breast specimen (also referred to herein as a "sample") and or performing digital tomosynthesis on an object. In one embodiment, the method and system includes an x-ray source, a flat panel digital x-ray detector, a specimen platform or container and a motion control mechanism configured for moving the source relative to the specimen (collectively referred to herein as the "unit"). The x-ray source is selectively energized to emit x-rays through the sample to the detector at selected positions of the source relative to the sample. The detector is controlled to collect projection x-ray images of the sample when the source is energized at the selected positions. One of the projection images is a two-dimensional image taken at standard imaging angle of 0°, and a tomosynthetic image reconstructed from a collection of tomosynthesis projection images is created.

In accordance with the aspects of the disclosed embodiments, the x-ray source moves around the stationary sample, typically, but not necessarily, in an arc. While the detector may rotate, in accordance with one aspect of the present disclosure, the detector remains stationary to maintain an equidistant center point. The x-ray data taken at each of a number of positions of the source relative to the sample is processed to form images, where two or more of the differing imaging positions are utilized to form a digital tomosynthesis image.

The collection of the tomosynthesis projection images is processed, typically using a computing device or other processor, into one or more reconstructed images representing a volume of the sample and relating to one or more image planes that are selectively the same or different from that of the 2-D image. The 2-D image and the reconstructed tomosynthesis images are selectively displayed.

The above allows the clinician verification via a display of either a three-dimensional or slice/multiplanar view of the sample that margins have been attained by the surgeon.

In a further aspect, the disclosed embodiments are directed to method and system for selectively using the same x-ray equipment to take, process and display a 2-D specimen radiography image and projection tomosynthesis images. In one embodiment, this includes an x-ray source, a flat panel digital x-ray detector, and a specimen platform or container and a motion control mechanism configured for moving the source relative to the specimen (collectively referred to herein as the "unit"). The x-ray source is selectively energized to emit x-rays through the sample or specimen to the detector at selected positions of the source relative to the sample. The detector is controlled to collect projections x-ray images of the sample when the source is energized at the selected positions. One of the projection images is a two-dimensional image taken at standard imaging angle of 0°. A tomosynthetic image reconstructed from a collection of projection images is created.

The above aspects of the disclosed embodiments overcome the deficiencies of the prior art by advantageously allowing the operator to be able to view the sample in a three-dimensional mode and take varying slices to ensure that the surgeon has attained a correct margin in an expedient manner without having to manipulate the excised sample.

In one aspect, the present disclosure is directed to a cabinet X-ray system. In one embodiment, the system includes an X-ray source, a flat panel digital X-ray detector, a specimen platform and a motion control mechanism configured for moving the source relative to the specimen or sample (collectively referred to herein as the "imaging unit"). The components of the system described above are disposed or contained in a cabinet.

In one embodiment, the X-ray source is selectively energized to emit X-rays through the sample to the detector at selected positions of the source relative to the sample. In one embodiment, a control unit or X-ray controller can be used to selective energize the X-ray source.

The detector is controlled to collect projection X-ray images of the sample when the source is energized at the selected positions. Preferably, one of the projection images is a two-dimensional image taken at a standard imaging angle of 0°. A tomosynthetic image reconstructed from a collection of tomosynthesis projection images is created.

The collection of the tomosynthesis projection images is processed, typically using a computing device or other processor, into one or more reconstructed images. The reconstructed images represent a volume of the sample and relate to one or more image planes that are selectively the same or different from that of the 2-D image. The 2-D image and the reconstructed tomosynthesis images are selectively displayed.

This allows the clinician verification via a display of either a three-dimensional or slice/multiplanar view of the sample that margins have been attained by the surgeon.

In a further aspect, the disclosed embodiments are directed to method and system for selectively using the same X-ray equipment to take, process and display a 2-D specimen radiography image and projection tomosynthesis images. In one embodiment, this includes an X-ray source, a flat panel digital X-ray detector, and a specimen platform or container and a motion control mechanism configured for moving the source relative to the specimen or sample (collectively referred to herein as the "unit"). The X-ray source is selectively energized to emit X-rays through the sample or specimen to the detector at selected positions of the source relative to the sample. The detector is controlled to collect projections X-ray images of the sample when the source is energized at the selected positions. One of the projection images is a two-dimensional image taken at standard imaging angle of 0° and a tomosynthetic image reconstructed from a collection of projection images is created.

The collection of the tomosynthesis projections images is processed by a computer or other processor into one or more reconstructed images representing a volume of the sample and relate to one or more image planes that are selectively the same or different from that of the 2-D specimen image. The 2-D specimen image and the reconstructed tomosynthesis images are selectively displayed.

The above aspects of the disclosed embodiments overcome the deficiencies of the prior art by advantageously allowing the operator to be able to view the sample in a three-dimensional mode and take varying slices to ensure that the surgeon has attained a correct margin in an expedient manner without having to manipulate the excised sample.

In a further aspect, the present disclosure relates to a cabinet system for performing X-ray digital Tomosynthesis on an object. In one embodiment, the cabinet system includes an imaging unit with an X-ray source; a digital X-ray detector; and a specimen platform positioned adjacent the digital X-ray detector and adapted to support an object thereon.

In one embodiment, the system includes a motion control mechanism to which the X-ray source is mounted is configured for moving the X-ray source along a path within the cabinet to selected positions relative to the object.

In one embodiment, the system includes an X-ray control unit configured to selectively energize the X-ray source to emit X-rays toward the object.

In one embodiment, the system includes a computer system coupled to and for controlling the digital X-ray detector, the motion control mechanism and X-ray control unit; wherein the computer system is configured to control the digital X-ray detector, the motion control mechanism and X-ray control unit and collect 2-D X-ray images of the object from the digital X-ray detector when the X-ray source is energized at the selected positions to create a collection of 2-D X-ray projection images. The computer system is further configured to process the collection of 2-D X-ray images into at least one reconstructed 3-D tomosynthesis image. A display or monitor is coupled to the computer to display the at least one reconstructed 3-D tomosynthesis image.

In another aspect, the present disclosure is directed to a method of cabinet X-ray digital imaging. In one embodiment, the method includes an imaging unit comprising an X-ray source, a digital X-ray detector, a specimen platform positioned adjacent the digital X-ray detector and adapted to support an imaging object thereon, a motion control mechanism to which the X-ray source is mounted that is configured for moving the X-ray source along a path to selected positions relative to the imaging, means of selectively energizing the X-ray source to emit X-rays toward the imaging object in communication with the X-ray source, a computer system in communication with the digital X-ray detector, the motion control mechanism and means of selectively energizing the X-ray source; wherein the computer system is configured to control the digital X-ray detector, the motion control mechanism and means of selectively energizing the X-ray source and collect 2-D X-ray images of the imaging object from the digital X-ray detector when the X-ray source is energized at the selected positions to create a collection of 2-D X-ray projection images.

In one embodiment, the computer system is configured to process the collection of 2-D X-ray images into at least one reconstructed 3-D tomosynthesis image including a volume of the imaging object or an image plane of the imaging object. The at least one reconstructed 3-D tomosynthesis image can be displayed.

These and other aspects and advantages of the exemplary embodiments will become apparent from the following detailed description considered in conjunction with the accompanying drawings. It is to be understood, however, that the drawings are designed solely for purposes of illustration and not as a definition of the limits of the invention, for which reference should be made to the appended claims. Moreover, the drawings are not necessarily drawn to scale and that, unless otherwise indicated, they are merely intended to conceptually illustrate the structures and procedures described herein. In addition, any suitable size, shape or type of elements or materials could be used.

DETAILED DESCRIPTION

The systems and methods of the present disclosure address the needs of the art by providing tomosynthesis apparatus and techniques for imaging breast specimens that overcome the shortfall of the data received from two-dimensional imaging systems. The aspects of the present disclosure enable the use of tomosynthesis to efficiently provide accurate three-dimensional imaging of a specimen in which overlapping images having differing attenuation characteristics by applying a three-dimensional reconstruction algorithm, all in an X-ray cabinet.

As used herein, the term "computer," "computer system" or "processor" refers to any suitable device operable to accept input, process the input according to predefined rules, and produce output, including, for example, a server, workstation, personal computer, network computer, wireless telephone, personal digital assistant, one or more microprocessors within these or other devices, or any other suitable processing device with accessible memory.

The term "computer program" or "software" refers to any non-transitory machine readable instructions, program or library of routines capable of executing on a computer or computer system including computer readable program code.

Specimen Tomography is a three-dimensional specimen imaging system. It involves acquiring images of a sample at multiple viewpoints, typically over an arc or linear path. The three-dimensional (3-D) image is constructed by the reconstruction of the multiple image data set.

Figure 1:
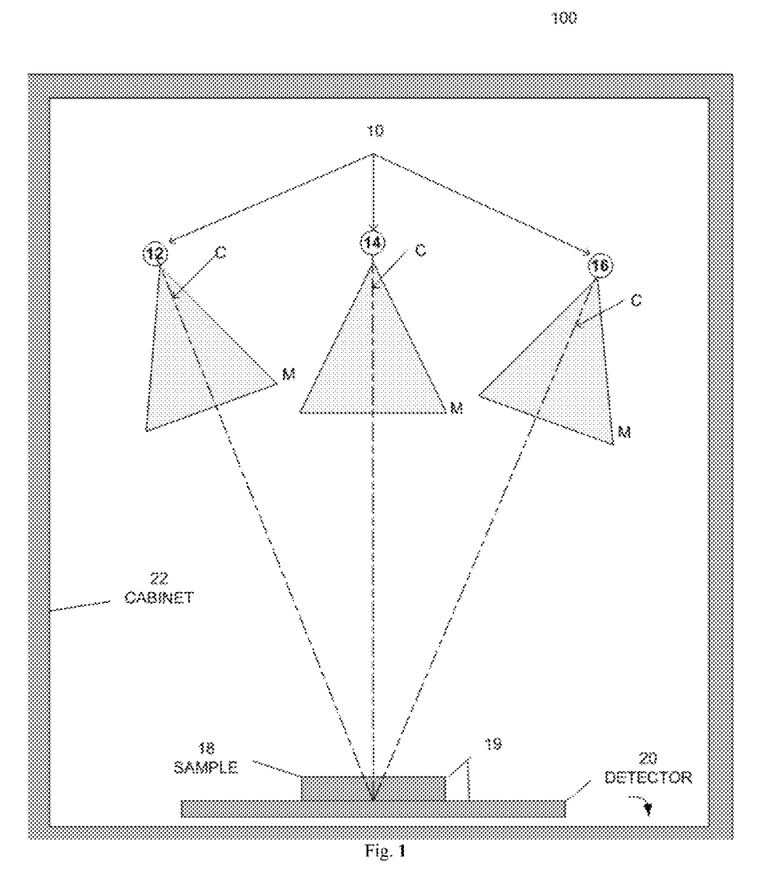
FIG. 1—Schematically illustrates a front view of an X-ray source, a specimen/sample, and a digital detector, where the X-ray source moves relative to the specimen for imaging the specimen at different angles, in one embodiment of a system incorporating aspects of the present disclosure.

One embodiment of a system 100 incorporating aspects of the present disclosure is illustrated in FIG. 1 The system 100 is totally enclosed or housed in an X-ray cabinet 22. In accordance with the aspects of the disclosed embodiments, the X-ray source 10 moves around the stationary sample 18, typically, but not necessarily, in an arc. References 12, 14 and 16 of FIG. 1 illustrate exemplary positions of the X-ray source 10 within the X-ray cabinet 22. The reference "C" at each of the positions 12, 14, 16 of the X-ray source 10 in FIG. 1 refers to the point source of the X-ray beam. The reference "M" refers to the spread or fan of the X-ray beam.

While the detector 20 may move or rotate, in accordance with one aspect of the present disclosure, the detector 20 remains stationary relative to the sample 18 and X-ray source 10 to maintain an equidistant center point. The X-ray data taken at each of a number of exemplary positions 12, 14, 16 of the X-ray source 10 relative to the sample 18 within the X-ray cabinet 22 is processed to form images, where two or more of the differing imaging positions are utilized to form a digital tomosynthesis image.

In one embodiment, the aspects of the present disclosure limit the arc or linear travel of the X-ray source 10 over about a 20° to about a 50° arc, preferably about 30°, more preferably about 20°. The movement can be clockwise or counter clockwise along a path, which includes for example, one or more, or a combination thereof, of the following exemplary ranges: between approximately 350° (reference position 12), to 0° (reference position 14) to 10° (reference position 16), or between approximately 340° (reference position 12) to 0° (reference position 14) to 20° (reference position 16) and or between approximately 335° (reference position 12) to 0° (reference position 14) to 25° (reference position 16). The ranges recited herein are intended to be approximate and inclusive of start and endpoints. In the example of FIG. 1 the detector 20 is stationary as is the sample 18. The sample 18, also referred to as the "object" or "imaging object" is disposed on or rests on the specimen platform 19 (which is a protective cover) or other surface of the detector 20.

In operation, X-ray source 10 is energized to emit an X-ray beam, generally throughout its travel along one or more of the paths or positions described above. The X-ray beam travels through the sample 18 to the detector 20 and the multiple images collected at varying angles are stored and then utilized for the tomosynthesis reconstruction. The X-ray source 10 may range from about 0 kVp to about 90 kVp, preferably a 50 kVp 1000 μa X-ray source.

Different embodiments of the present disclosure can utilize different ranges of motion of one or more of the X-ray source 10 and detector 20 as well as changing the angularity of one or both. The inventive aspects of the present disclosure differ from the prior art in that in prior art systems either the detector and X-ray source 10 and/or the isocenter is above the sample and not at the detector surface. In accordance with the aspects of the present disclosure, in one embodiment, the X-ray source 10 is configured to move, as is described herein, while the detector 20 is configured to remain stationary or in a fixed position.

The detector 20 and associated electronics generate image data in digital form for each pixel at each of the angular positions 12, 14, 16 of X-ray source 10 and translation positions of the detector 20 relative to the sample 18. While only three positions 12, 14, 16 are illustrated in FIG. 1, in practice more images are taken at differing angles. For example, in one embodiment, images can be taken at approximately every 1° of rotation or motion of source 10.

Figure 2:
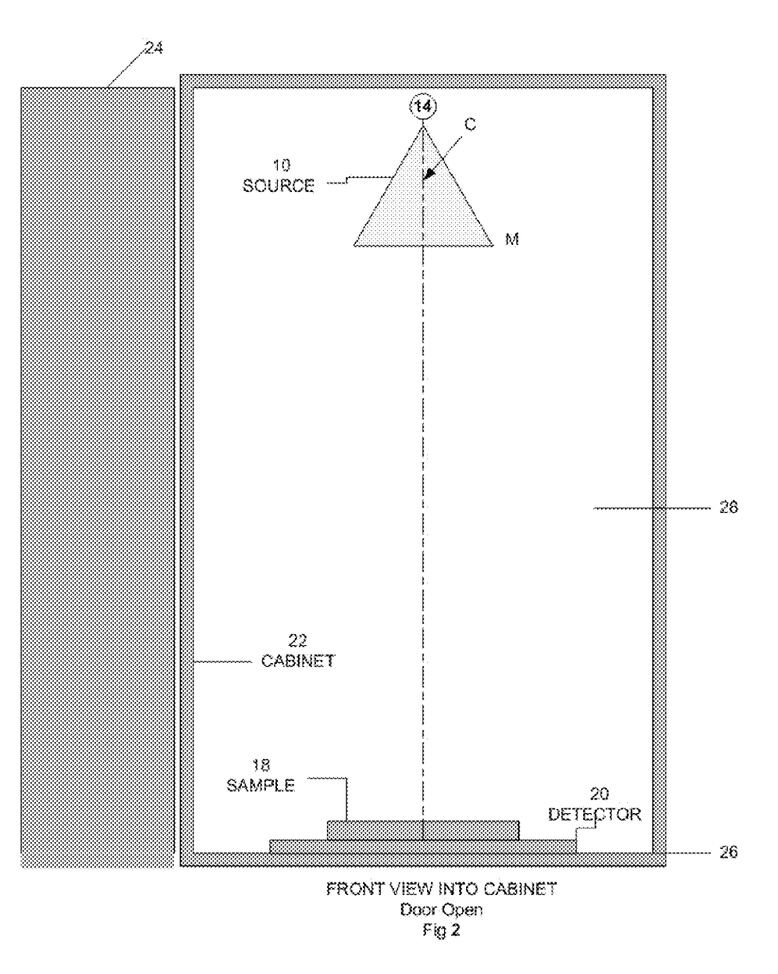
FIG. 2—Schematically illustrates an exemplary orientation of the X-ray source, specimen, and digital detector as viewed when the door of the cabinet is open, in one embodiment of a system incorporating aspects of the present disclosure.

FIG. 2 schematically illustrates one embodiment of the orientation of the X-ray source 10 as seen when the door 24 is opened and the X-ray source 10 is locate at approximately 0°, reference point 14 in this example, within the X-ray cabinet 22. In this embodiment, the motion of the X-ray source 10 can generally occur from the back to the front of the X-ray cabinet 22 with the detector 20 oriented, or otherwise disposed, at the base 26 of the X-ray cabinet 22, within the X-ray cabinet chamber 28. In one embodiment, the detector 20 is suitably coupled to the base 26 of the X-ray cabinet 22. The X-ray spread in this example can be from about 0 kVp to about 50 kVp with the system preferably utilizing an AEC (Automatic Exposure Control) to ascertain the optimal setting to image the object or sample 18 being examined.

In one embodiment, the detector 20, X-ray source 10, and the swing arm 60 (FIG. 5) servo mechanism are controlled via a combination of one or more of software and hardware, such as non-transitory machine readable instructions stored in a memory that are executable by one or more processors. On example of such a configuration can include controller cards of a computer 470 (FIG. 4), such as a MS Windows based computer. In one embodiment, non-transitory machine readable instructions being executed by one or more processors of the computer 470 is utilized to compile data received from the detector 20 and present resulting images to a suitable display or monitor 472 (FIG. 4) at each imaging position, such as positions 12, 14 and 16 shown in FIG. 1, the detector 20 generates the respective digital values for the pixels in a two-dimensional array. The size of detector 20 may range, for example, from about 5.08 centimeters by 5.08 centimeters to about 40.64 centimeters by 40.64 centimeters, preferably about 12.7 centimeters by 15.24 centimeters. In one example, detector 20 has a rectangular array of approximately 1536×1944 pixels with a pixel size of 74.8 micrometers. The image dataset attained at each respective position may be processed either at the full spatial resolution of detector 20 or at a lower spatial resolution by overlapping or binning a specified number of pixels in a single combined pixel value.

For example, if we bin at a 2×2 ratio, then there would be an effective spatial resolution of approximately 149.6 micrometers. This binning may be achieved within the original programming of the detector 20 or within the computer 470 providing the tomosynthetic compilation and image.

Figure 3:
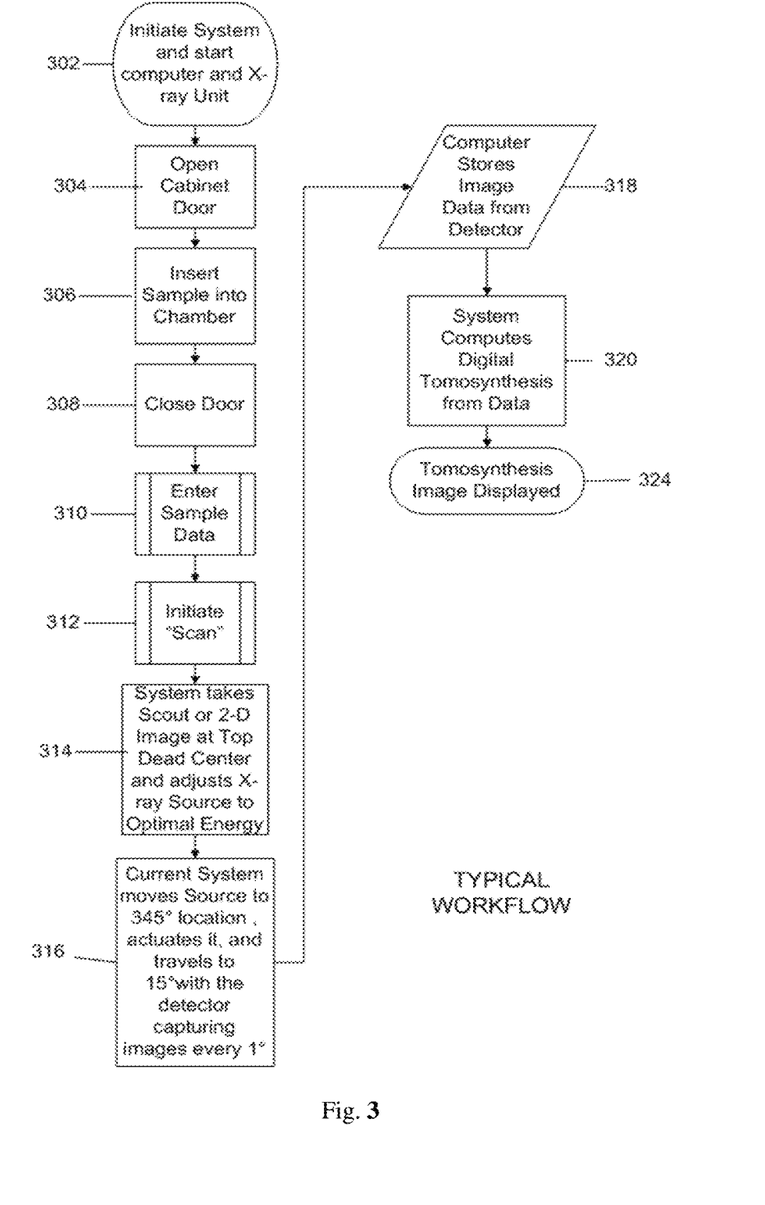
FIG. 3—Displays an exemplary workflow/flowchart of an aspect of the disclosed embodiments.

FIG. 3 illustrates one embodiment of an exemplary workflow from initiating 302 the system 100 through imaging, reconstruction and display 324 of data images collected of the sample 18.

As will be generally understood, the system 100 is initiated 302, the X-ray cabinet door 24 opened 304, and the sample 18 placed into 306 the X-ray cabinet chamber 28. As shown in FIG. 2, for example, the sample 18 is positioned on the detector 20 in a suitable manner. The door 24 is closed 308.

The data and information regarding the sample 18, including any other suitable information or settings relevant to the imaging process and procedure, is entered 310 into the computer 470. The scan is initiated 312. The system 100 will take 314 scout or 2-D images at Top Dead Center, which for purposes of this example is position 14 of FIGS. 1 and 2. The X-ray source 10 can then be moved to other positions, such as positions 12 and 16, and the detector 20 can be used to capture 316 images at various increments along the travel path of the X-ray source 10, such as about every 1 degree.

The captured images are stored 318 and digital tomosynthesis is performed 320. The tomosynthesis image is then displayed 324.

Figure 4:
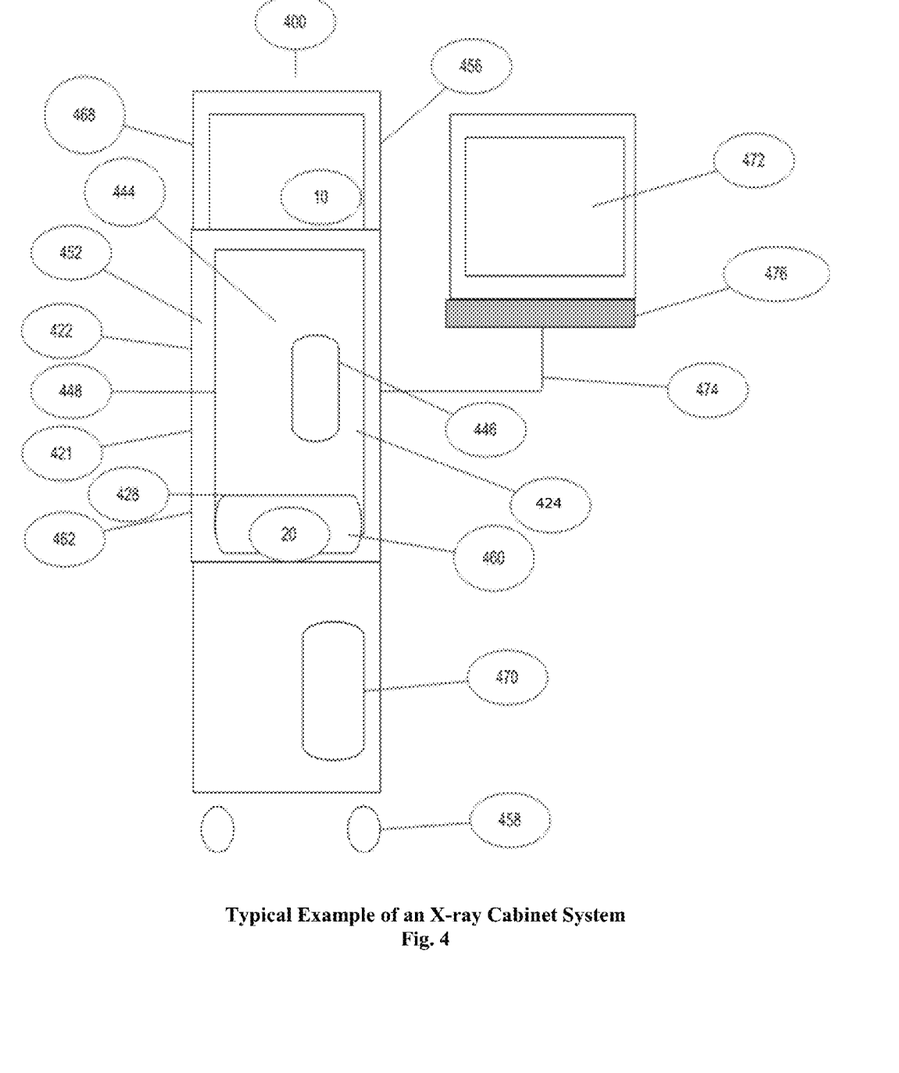
FIG. 4—Displays an example of an X-ray Cabinet System incorporating aspects of the present disclosure.

FIG. 4 shows one embodiment of an X-ray Cabinet System 400 incorporating aspects of the present disclosure. In this embodiment, the X-ray Cabinet System 400 is mounted on wheels 458 to allow easy portability. In alternate embodiments, the X-ray Cabinet System 400 can be mounted on any suitable base or transport mechanism. The cabinet 422 in this example, similar to the exemplary X-ray cabinet 22 of FIG. 1, is constructed of a suitable material such as steel. In one embodiment, the cabinet 422 comprises painted steel defining a walled enclosure with an opening or cabinet chamber 428. Within the cabinet chamber 428, behind door 424, resides an interior space forming a sample chamber 444, which in this example is constructed of stainless steel. Access to the sample chamber 444 is via an opening 446. In one embodiment, the opening 446 of the sample chamber 444 has a suitable door or cover, such as a moveable cover 448. In one embodiment, the moveable cover 448 comprises a door which has a window of leaded glass.

Between the outer wall 421 of cabinet 422 and the sample chamber 444 are sheets of lead 452 that serve as shielding to reduce radiation leakage emitted from the X-ray source 10. In the example of FIG. 4, the X-ray source 10 is located in the upper part 456 of the cabinet 422, in the source enclosure 468. The detector 20 is housed in the detector enclosure 460 at an approximate midpoint 462 of the cabinet 422.

Figure 5:
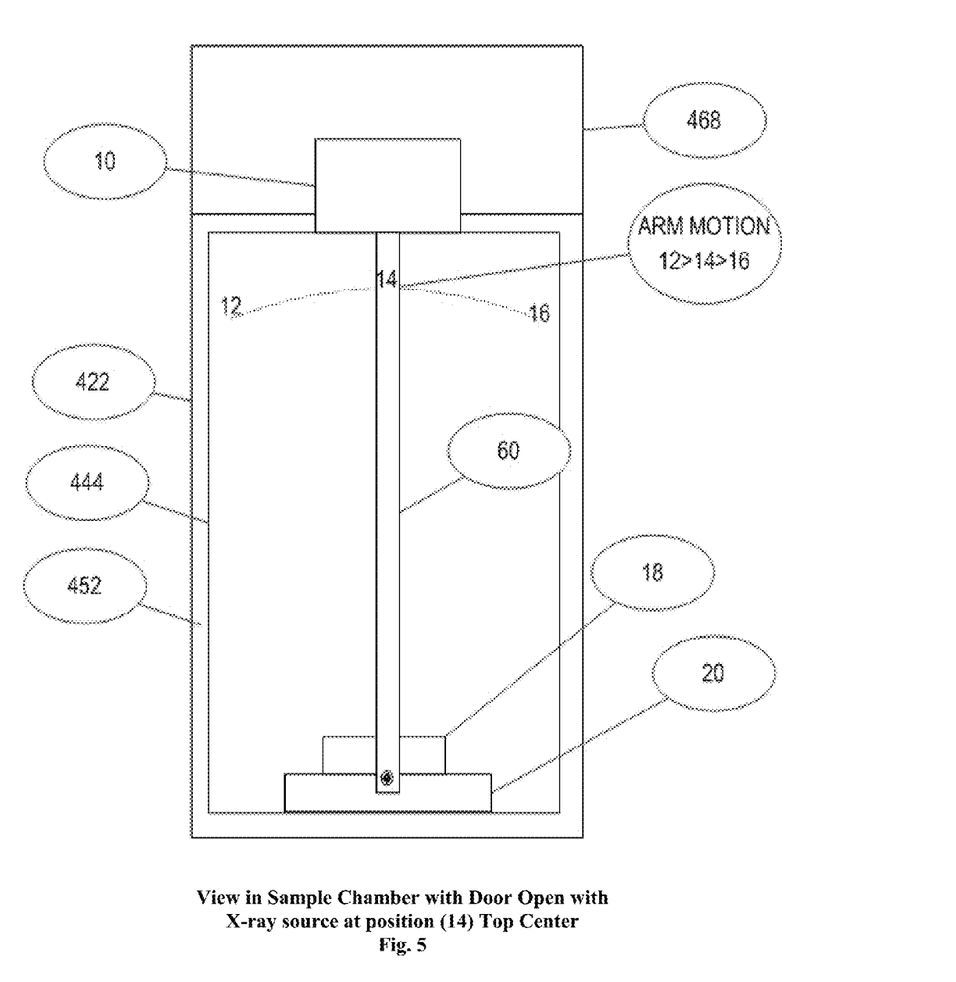
FIG. 5—Displays the sample chamber of the embodiment of FIG. 4 with the swing arm and a detector.
Figure 6:
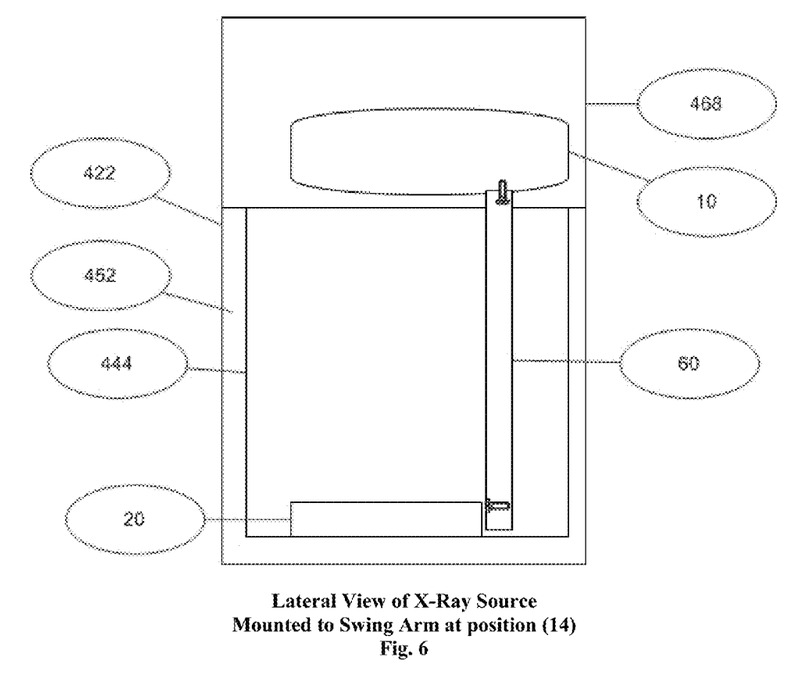
FIG. 6—Displays the lateral view of the X-ray source of the embodiment of FIG. 4 mounted to the top of the swing arm.

In one embodiment, a controller or computer 470 controls the collection of data from the detector 20, controls the swing arm 60 shown in FIGS. 5 & 6, and X-ray source 10. A monitor 472 displays the compiled data and can, for example, be mounted on an articulating arm 474 that is attached to the cabinet 422. The computer 470 receives commands and other input information entered by the operator via a user interface 476, such as a keyboard and mouse for example. In one embodiment, the computer 470 can comprise a touch screen or near touch screen device. Although the aspects of the disclosed embodiments will generally be described with respect to a computer 470, it will be understood that the computer 470 can comprise any suitable controller or computing device. Such computing devices can include, but are not limited to, laptop computers, mini computers, tablets and pad devices.

The computer 470 can be configured to communicate with the components of the X-ray cabinet system 400 in any suitable manner, including hardwired and wireless communication. In one embodiment, the computer 470 can be configured to communicate over a network, such as a Local Area Network or the Internet.

FIG. 5 shows a front interior view and FIG. 6 shows a lateral interior view of the sample chamber of imaging unit cabinet of FIG. 4. In this embodiment, a sample 18 is placed or otherwise disposed onto the detector 20. Using the computer 470 shown in FIG. 4, the operator enters in the parameters for the scan via the user interface 476, which can be displayed on the monitor 472. As used herein, the term "display" or "monitor" means any type of device adapted to display information, including without limitation CRTs, LCDs, TFTs, plasma displays, LEDs, and fluorescent devices. The computer 470 then sends the appropriate commands to the X-ray source 10 and detector 20 to activate image collection while the swing arm 60 is moving along a path or arc from position 14 to 12 to 16 (which are shown in FIGS. 1 and 5) or vice versa as described, which in this embodiment are at 345°, 0°, and 15° respectively with 0° at top dead center. At the end of the travel of the swing arm 60 at either position 12 or 16, the computer 470 issues the command to the X-ray source 10 and the detector 20 to cease operating. The individual 2-dimensional (2-D) images which were collected, in this example at 1° increments, are then tabulated in the computer 470 to create the tomosynthetic images. In one embodiment, the operator may select which images they wish via the user interface 476 as they are being displayed on the monitor 472. In one embodiment, the devices and components of the X-ray cabinet system 400 are suitably communicatively coupled together, including one or more of hard wire connections or wireless connections using a suitable wireless connection and communication transmission protocol, as will generally be understood. The X-ray cabinet system 400 can also be configured to transfer images via USB, CD-Rom, or WIFI.

Figure 7A:
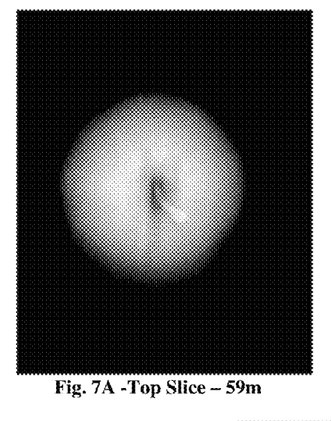
FIGS. 7A, 7B and 7C—Displays the results of the imaging of an apple at multiple depth cuts after tomosynthesis reconstruction in a cabinet X-ray system incorporating aspects of the present disclosure.
Figure 7B:
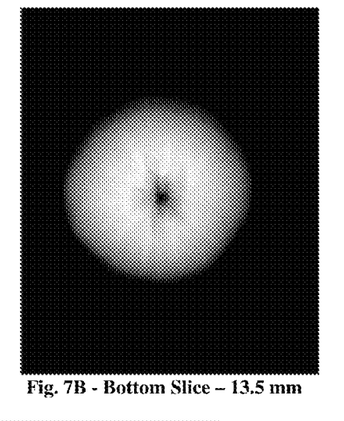
Figure 7C:
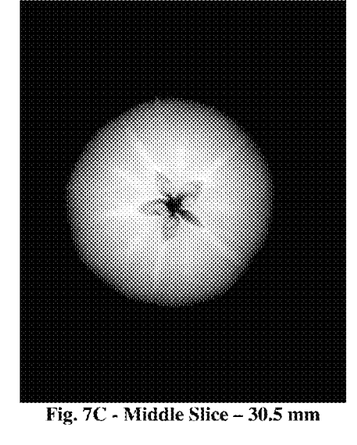

The dynamic imaging software of the disclosed embodiments reconstructs three-dimensional images (tomosynthesis) from two-dimensional projection images in real-time and on-demand. The software offers the ability to examine any slice depth, tilt the reconstruction plane for multiplanar views and gives higher resolution magnifications. FIGS. 7A, 7B, and 7C illustrate exemplary images of an apple using the above process.

FIG. 7A is an image of a slice of the apple at it's very top. 59 mm from the bottom. FIG. 7B is an image of an apple computed at 30.5 mm up from the detector, and FIG. 7C is a view of the apple computed at 13.5 mm from the bottom.

The real-time image reconstruction of the present disclosure enables immediate review, higher throughput, and more efficient interventional procedures reducing patient call backs and data storage needs. Multiplanar reconstruction enables reconstruction to any depth, magnification and plane, giving the viewer the greater ability to view and interrogate image data, thereby reducing the likelihood of missing small structures. Built-in filters allow higher in-plane resolution and image quality during magnification for greater diagnostic confidence. Software is optimized for performance using GPU technology.

The reconstruction software used in conjunction with the aspects of the present disclosure provides the users greater flexibility and improved visibility of the image data. It reconstructs images at any depth specified by the user, rather than at fixed slice increments. With fixed slice increments, an object located between two reconstructed slices, such as a calcification, is blurred and can be potentially missed. The aspects of the present disclosure provide for positioning the reconstruction plane so that any object is exactly in focus. This includes objects that are oriented at an angle to the detector 20. The aspects of the present disclosure provide for the reconstruction plane to be angled with respect to the detector plane.

Thus, while there have been shown and described and pointed out fundamental novel features of the invention as applied to the exemplary embodiments thereof, it will be understood that various omissions and substitutions and changes in the form and details of devices illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

What is claimed is:

1. A cabinet x-ray system for of obtaining x-ray images, projection x-ray images, and reconstructed tomosynthetic x-ray images of a specimen, the system comprising:
   a cabinet defining an interior chamber;
   an x-ray source;
   an x-ray detector;
   a specimen platform which is a protective cover of and in physical contact with the x-ray detector;
   a motion control mechanism configured for moving the x-ray source to or along a plurality of positions within the interior chamber relative to the specimen disposed on the specimen platform; and
   a controller configured to:
      selectively energize the x-ray source to emit x-rays through the specimen to the x-ray detector at selected positions of the x-ray source relative to the specimen such that the isocenter of the emitted x-rays at the selected positions is located at a surface of the x-ray detector;
      control the x-ray detector to collect projection x-ray images of the specimen when the x-ray source is energized at the selected positions, wherein one of the projection x-ray images is a two-dimensional x-ray image taken at standard imaging angle of approximately 0°;
      create a tomosynthetic x-ray image reconstructed from a collection of projection x-ray images;
      process the collection of the projection x-ray images in the controller into one or more reconstructed tomosynthetic x-ray images representing a volume of the specimen and relating to one or more image planes that are selectively the same or different from that of the two-dimensional x-ray image; and
      selectively display the two-dimensional x-ray image and the one or more reconstructed tomosynthetic x-ray images.

2. The cabinet x-ray system of claim 1, wherein the cabinet comprises a walled enclosure surrounding the interior chamber, a door configured to cover the interior chamber and a sampling chamber within the interior chamber for containing the specimen.

3. The cabinet x-ray system of claim 1, wherein the specimen platform is configured for excised tissue, organ or bone specimens.

4. The cabinet x-ray system of claim 1, wherein the specimen platform is configured for any organic or inorganic specimen that fits inside an x-ray cabinet.

5. The cabinet x-ray system of claim 1, further comprising a tomosynthesis mechanism mounted in the cabinet.

6. The cabinet x-ray system of claim 1, wherein the x-ray source is a moveable x-ray source, the cabinet x-ray system including a device to move or position the x-ray source within the cabinet.

7. The cabinet x-ray system of claim 1, wherein the motion control mechanism is configured to move the x-ray source along a path substantially defining an arc.

8. The cabinet x-ray system of claim 1, wherein the x-ray detector is in a stationary or fixed position within the cabinet.

9. The cabinet x-ray system of claim 1, wherein the motion control mechanism is configured to move the x-ray source along a path in a range from about 350° to 10° or from about 340° to 20° or vice versa or a maximum of about 335° to 25° or vice versa.

10. The cabinet x-ray system of claim 9, wherein the motion control mechanism is configured to move the x-ray source from back to front or front to back in the cabinet.

11. The cabinet x-ray system of claim 9, wherein a movement of the x-ray source within the cabinet is from side to side along a path such that the spread of the x-ray beam along the path is within the spread of the x-ray beam when the x-ray source is at the standard imaging angle of about 0°.

12. The cabinet x-ray system of claim 1, in which the x-ray source is a minimum 50 kVp and 1000 μa X-ray source.

13. The cabinet x-ray system of claim 1, in which the x-ray source is a micro-focus X-ray source.

14. The cabinet x-ray system of claim 1, wherein the x-ray detector comprises a CMOS x-ray detector.

15. The cabinet x-ray system of claim 1, wherein the controller is configured to supply standard two-dimensional x-ray images.

16. The cabinet x-ray system of claim 1, in which the controller is configured to interpolate the projection x-ray images gathered and calculate a tomosynthetic x-ray image.

17. The cabinet x-ray system of claim 1, wherein the controller comprises computer readable program code or non-transitory machine readable instructions, which when executed by one or more processors of the controller, is configured to provide built-in filters allowing higher in-plane resolution and image quality of the tomosynthetic x-ray images during magnification for greater diagnostic confidence.

18. The cabinet x-ray system of claim 1, wherein the controller is configured to reconstruct three-dimensional tomosynthetic x-ray images from two-dimensional projection x-ray images in real-time and on-demand.

19. The cabinet x-ray system of claim 1, wherein the controller includes graphic processor unit (GPU) technology and is configured to deliver real-time three-dimensional image reconstruction of tomosynthetic x-ray images by utilizing graphic processor unit (GPU) technology.

20. The cabinet x-ray system of claim 1, wherein the specimen platform is configured for a breast specimen of a person.

21. The cabinet x-ray system of claim 1, wherein the x-ray detector is movable within the cabinet.

22. The cabinet x-ray system of claim 1, wherein the x-ray detector comprises a flat panel digital x-ray detector.

23. A method for obtaining x-ray images of a specimen in a cabinet x-ray system, processing and displaying a two-dimensional x-ray image and projection x-ray images of the specimen, wherein the cabinet x-ray system comprising a cabinet defining an interior chamber; an x-ray source, an x-ray detector, a specimen platform which is a protective cover of and in physical contact with the x-ray detector, and a motion control mechanism configured for moving the x-ray source to or along a plurality of positions within the interior chamber relative to the specimen disposed on the specimen platform; and a controller configured to selectively energize the x-ray source to emit x-rays through the specimen to the x-ray detector at selected positions of the x-ray source relative to the specimen, wherein the method comprises:

controlling the x-ray detector to collect projection x-ray images of the specimen when the x-ray source is energized at the selected positions such that the iso-center of the emitted x-rays at the selected positions is located at a surface of the x-ray detector, wherein one of the projection x-ray images is a two-dimensional x-ray image taken at standard imaging angle of approximately 0°;

creating a tomosynthetic x-ray image reconstructed from a collection of projection x-ray images;

processing the collection of the projection x-ray images in the controller into one or more reconstructed tomosynthetic x-ray images representing a volume of the specimen and relating to one or more image planes that are selectively the same or different from that of the two-dimensional x-ray image; and selectively displaying the two-dimensional x-ray image and the one or more reconstructed tomosynthetic x-ray images.

24. The method of claim 23, comprising concurrently displaying the two-dimensional x-ray image and the one or more reconstructed tomosynthetic x-ray images.

25. The method of claim 23, wherein the specimen comprises excised tissue, organ or bone specimen.

26. The method of claim 23, wherein the specimen comprises organic or inorganic specimens that are suitably sized to fit within the interior chamber of the cabinet.

27. The method of claim 23, wherein the cabinet x-ray system comprises a tomosynthesis mechanism mounted in the cabinet of the cabinet x-ray system.

28. The method of claim 23, comprising using the controller to move the x-ray source to a plurality of positions within the cabinet along a path defining an arc.

29. The method of claim 23, further comprising maintaining the x-ray detector in a stationary or fixed position within the cabinet, while moving the x-ray source to one or more positions within the cabinet.

30. The method of claim 23, further comprising moving the x-ray source along a path within the cabinet, where the x-ray source is moved on the path along a range from about 350° to 10° or from about 340° to 20° or vice versa or a maximum of about 335° to 25° or vice versa.

31. The method of claim 23, further comprising moving the x-ray source within the cabinet from back to front or front to back.

32. The method of claim 23, further comprising moving the x-ray source within the cabinet from side to side along a path such that the spread of an x-ray beam along the path is within the spread of the x-ray beam when the x-ray source is at the standard imaging angle of about 0°.

\* \* \* \* \*